US011385229B2

(12) United States Patent
Murthy et al.

(10) Patent No.: US 11,385,229 B2
(45) Date of Patent: Jul. 12, 2022

(54) AMPLIFICATION TECHNOLOGY USING DUAL ENZYME CASCADE DETECTION

(71) Applicant: The Regents of the University of California, Oakland, CA (US)

(72) Inventors: Niren Murthy, Berkeley, CA (US); Lee W. Riley, Berkeley, CA (US); Tara Renee BeBoer, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 20 days.

(21) Appl. No.: 16/541,111

(22) Filed: Aug. 14, 2019

(65) Prior Publication Data

US 2019/0376972 A1    Dec. 12, 2019

Related U.S. Application Data

(63) Continuation of application No. PCT/US2018/018548, filed on Feb. 17, 2018.

(60) Provisional application No. 62/461,190, filed on Feb. 20, 2017.

(51) Int. Cl.
*G01N 33/573* (2006.01)

(52) U.S. Cl.
CPC .................. *G01N 33/573* (2013.01)

(58) Field of Classification Search
None
See application file for complete search history.

(56) References Cited

U.S. PATENT DOCUMENTS

2005/0227309 A1* 10/2005 Corry ................... G01N 33/581
435/32

FOREIGN PATENT DOCUMENTS

WO    WO-2008066832 A2 *  6/2008 ......... G01N 33/5308

OTHER PUBLICATIONS

Van Berkel, S.S. et al. 2013. Assay platform for clinically relevant metallo-B-lactamases. Journal of Medicinal Chemistry 56: 6945-6953. specif. pp. 6945, 6946, 6947, 6948.*
Ferraz, C.C. et al. 2014. Validation of in vitro analytical method to measure papain activity in pharmaceutical formulations. International Journal of Pharmacy and Pharmaceutical Sciences 6(2): 658-661. specif. p. 658.*
Singh, R. et al. 1993. An amplified assay for thiols based on reactivation of papain. Analytical Biochemistry 213: 49-56. specif. pp. 49, 51, 52.*
Gallah, S. et al. 2014. The B-Lacta Test for direct detection of extended-spectrum B-lactamase-producing Enterobacteriaceae in urine. Journal of Clinical Microbiology 52(10): 3792-3794. specif. p. 3792.*
Buckwell, S.C. et al. 1988. Hydroysis of 3-substituted cephalosporins catalyzed by Beta-lactamases I and II from Bacillus cereus and by hydroxide ion. Journal of the Chemical Society, Perkin Transactions 2, pp. 1823-1827. specif. pp. 1823, 1825, 1826.*
Doi, M. et al. 1987. Purification and characterization of two benzoyl-L-tyrosine-p-nitroanilide hydrolases from etiolated leaves of *Zea mays* L. Plant Physiology 84: 770-774. specif. p. 770.*

* cited by examiner

*Primary Examiner* — Renee Claytor
*Assistant Examiner* — Sharon M. Papciak
(74) *Attorney, Agent, or Firm* — Richard Aron Osman

(57) ABSTRACT

Diagnostic assays and methods employ a dual-enzyme cascade system comprised of two enzymatic amplifiers and two molecular probes, by (a) incubating a target enzyme with a target enzyme substrate to liberate a thiol; (b) incubating the thiol with a disulfide inactivated amplification enzyme to activate the amplification enzyme in an interchange reaction of the thiol and the disulfide; and (c) incubating the activated amplification enzyme with an amplification enzyme substrate to generate an amplified signal.

1 Claim, 8 Drawing Sheets

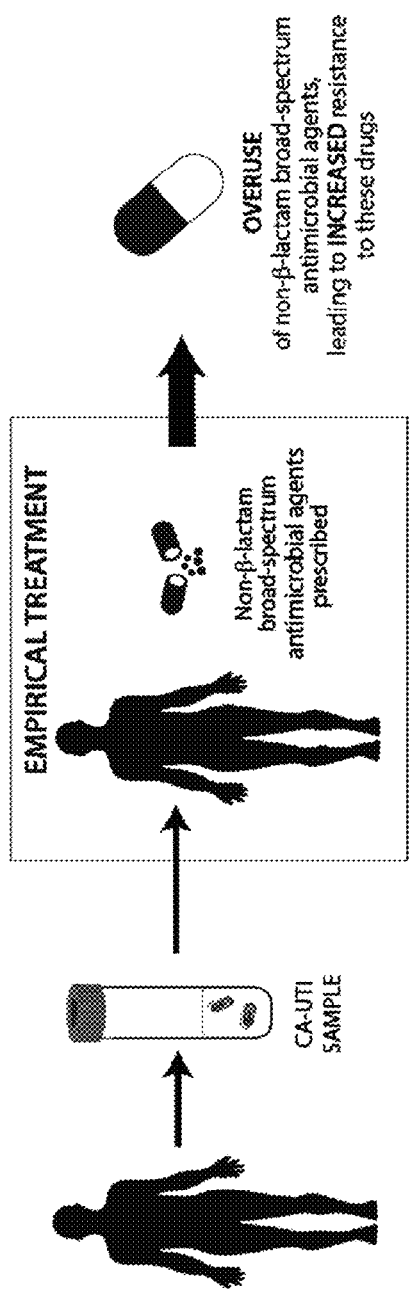
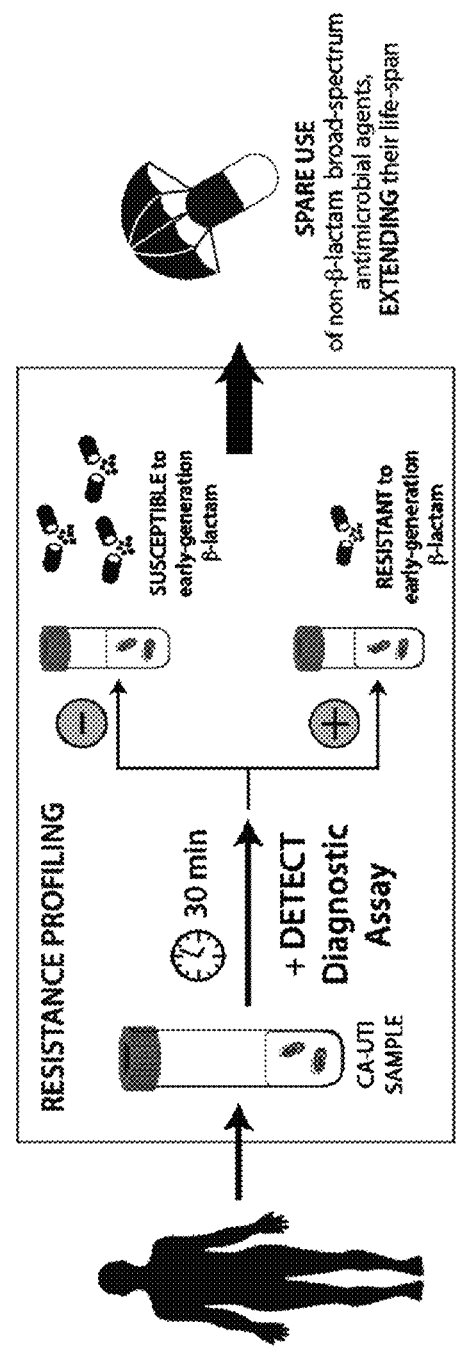

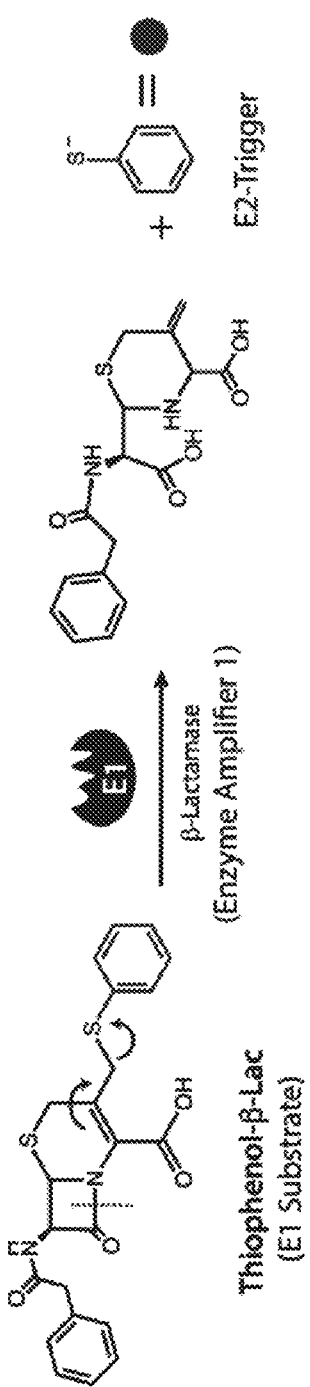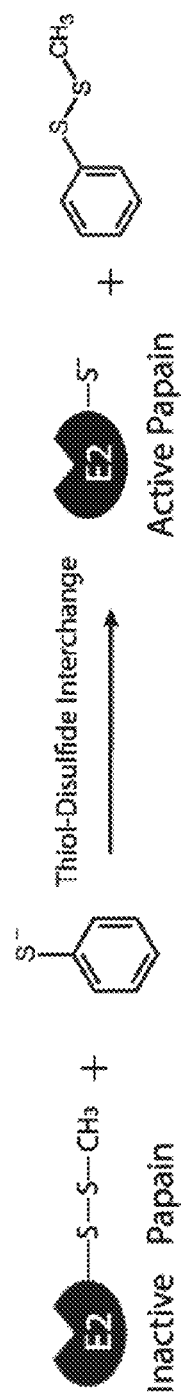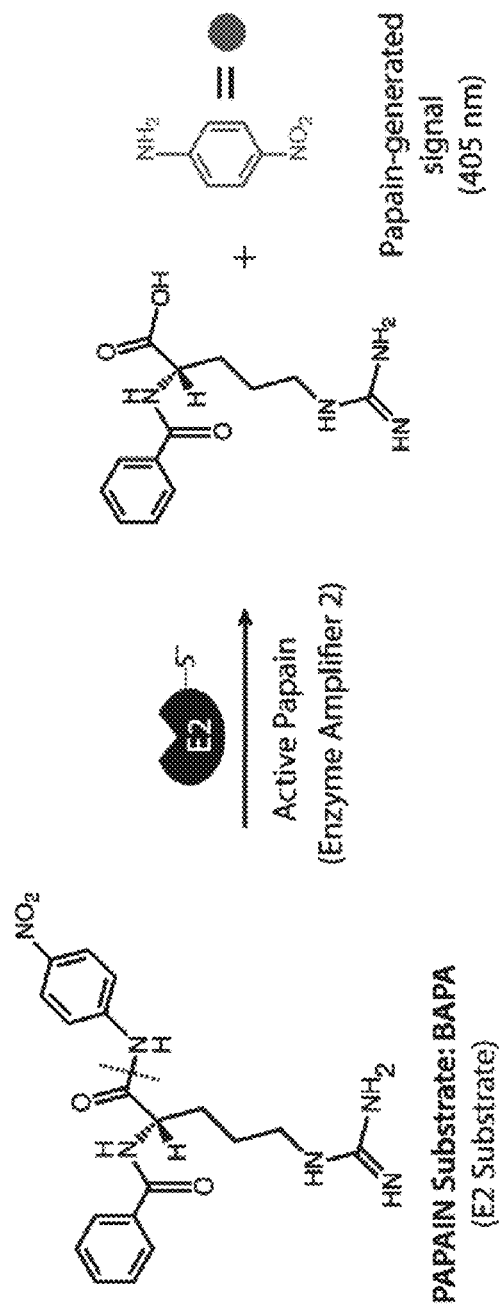
Fig 2B
Fig 2C
Fig 2D

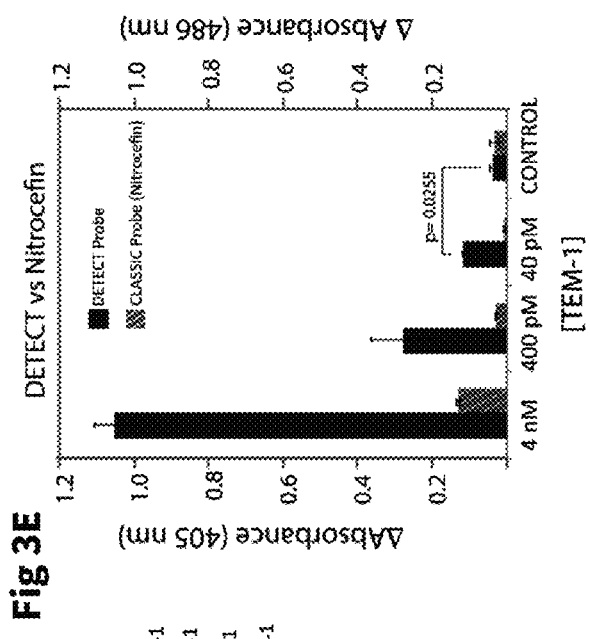
Fig 3B
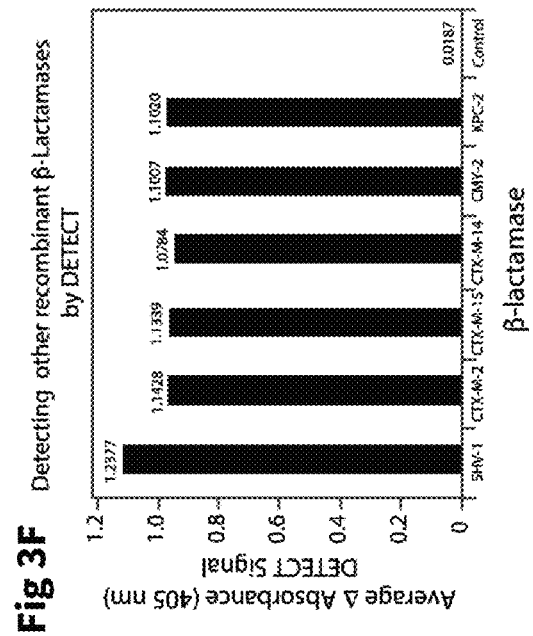
Fig 3E
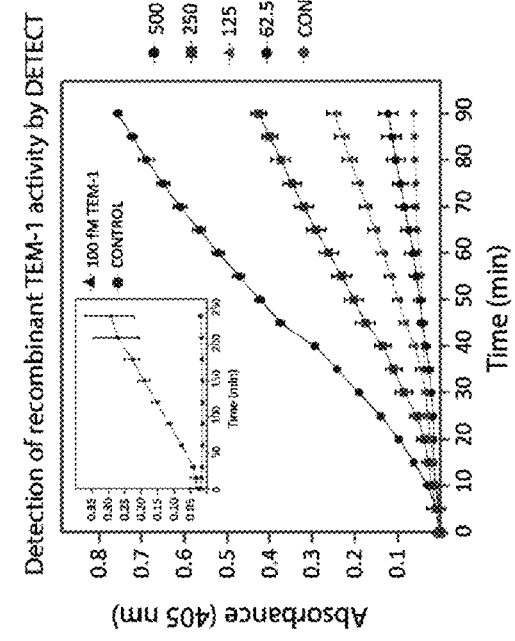
Fig 3C
Fig 3D
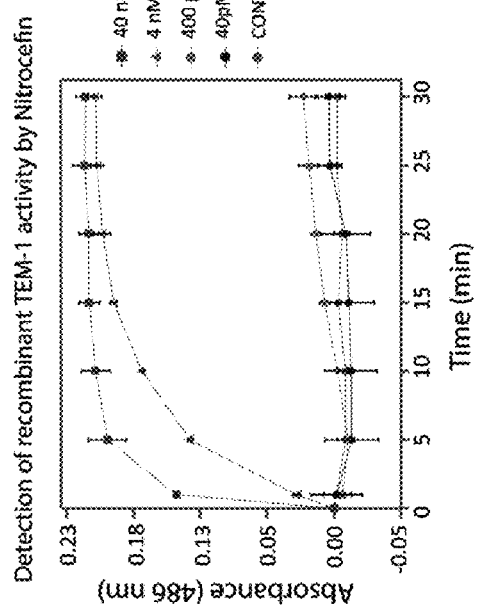
Fig 3F

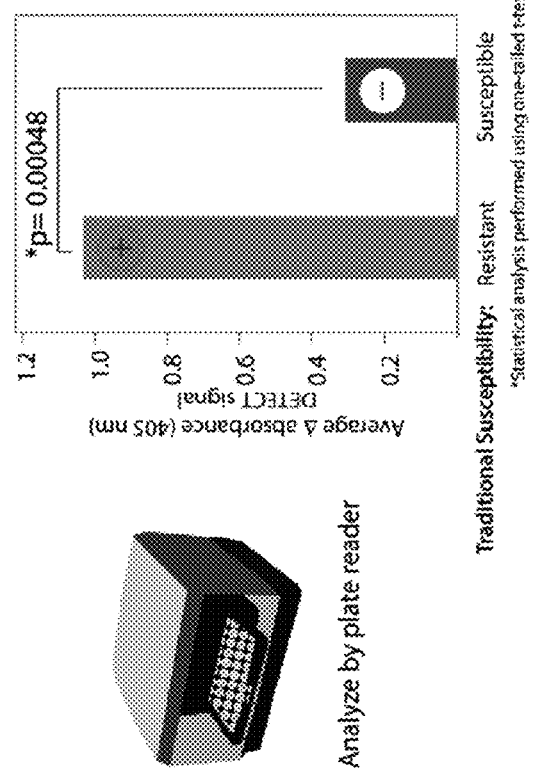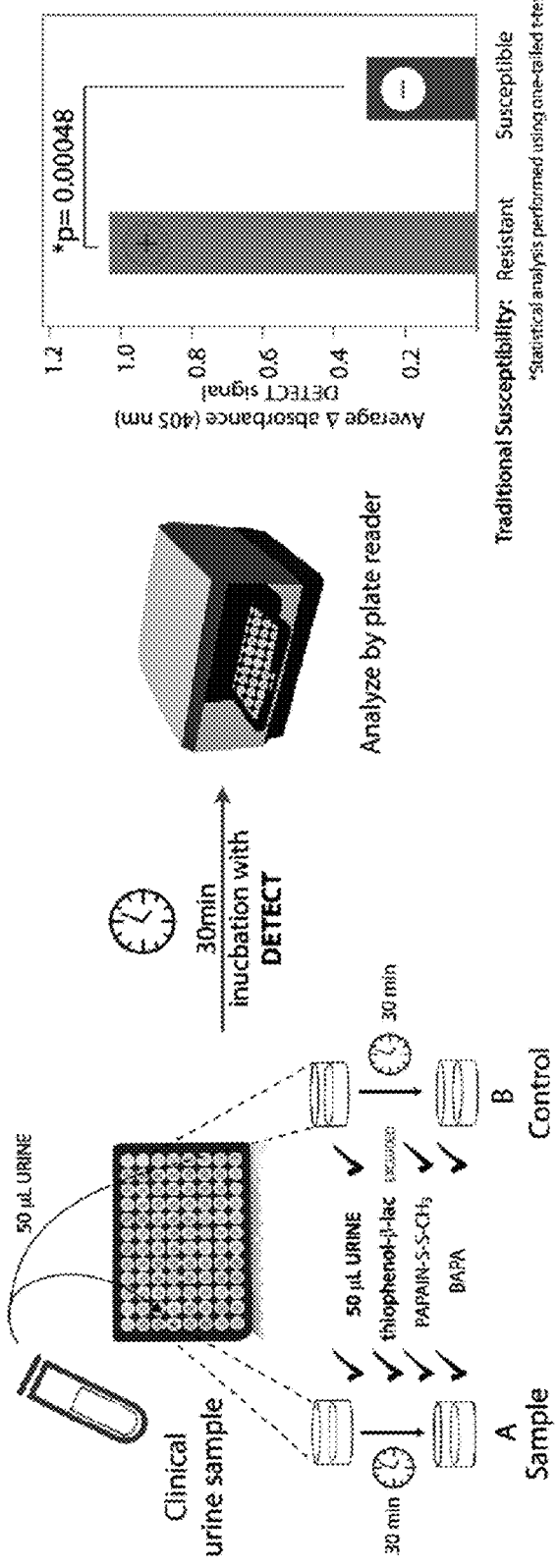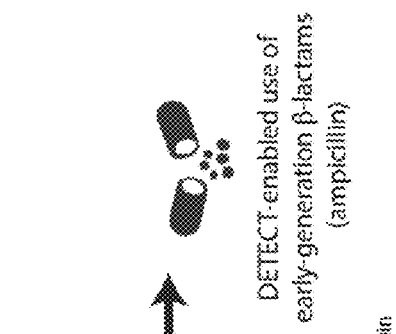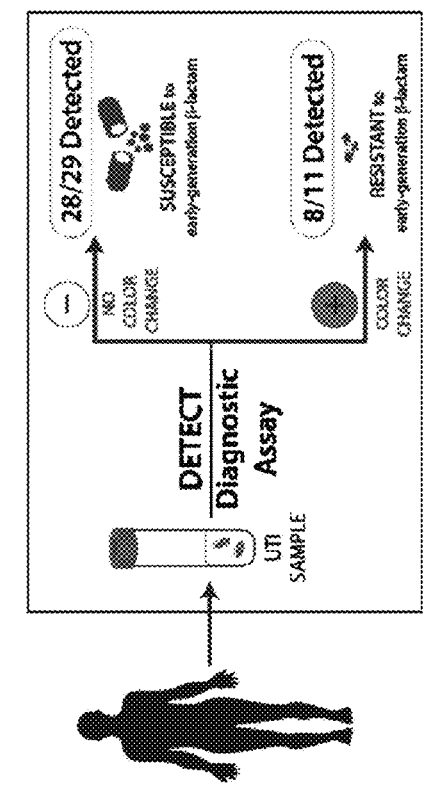

AMPLIFICATION TECHNOLOGY USING DUAL ENZYME CASCADE DETECTION

This invention was made with government support under Grant Number AI117064 awarded by the National Institutes of Health. The government has certain rights in the invention.

INTRODUCTION

It has been projected that deaths attributed to drug-resistant infections will surpass 10 million by 2050, with estimated associated costs reaching $100 trillion USD of the global GDP. β-lactam antibiotics represent one of the most frequently prescribed classes of pharmaceuticals worldwide, where 22.0 standard units of antibiotics are prescribed per person in the US in 2010. As such, the overuse of antibiotics is a significant driver directing the spread of antibiotic resistance, and therefore, represents a significant factor that must be addressed in efforts to combat this growing epidemic. Unfortunately, symptomatic treatment of infectious diseases with antibiotics remains standard practice across the globe due to an absence of point-of-care diagnostic tools.

Because the number of bacteria required to induce conditions of infectious disease are low, ranging from 10 CFU/mL to 10,0000 CFU/mL (CFU, colony forming units), detection of the enzymes expressed by these bacteria that confer antibiotic resistance require time-consuming culturing and/or expensive analytical instrumentation.

Advanced instrumentation such as PCR, matrix-assisted laser desorption ionization mass spectrometry, and microscopy has been considered as an approach to enhance detection limits of bacterial pathogens, however this strategy is only practical for the developed world. Because the vast majority of people suffering from and contributing to the propagation of antibacterial resistance reside in underdeveloped countries, alternative options must be developed. Molecular probes represent a feasible option because unlike nucleic acid based diagnostic methods they are simple, rapid, and do not require sophisticated instrumentation or skilled personnel.

β-lactamases represent a particularly interesting diagnostic target because they direct resistance to β-lactam antibiotics and their presence in a patient sample can significantly influences clinical decision making. While efforts have been made to create biochemical assays to detect the activity of β-lactamases using chromogenic, fluorogenic, or chemiluminescent chemical probes, translation of this approach to clinical settings has been limited by poor sensitivity.

More recently, biochemical kit Rapidec became available for use in medical laboratories and has shown incredible power in detecting carbapenemases-producing Enterobacteriaceae. The use of Rapidec for the detection of carbapenamase-producing clinical isolates features a modest sensitivity limit because it utilizes a pH indicator-based detection system and requires overnight culturing to and sample preparation.

Other relevant assays include: an amplified assay for thiols based on reactivation of papain, Singh et al., Anal Biochem (1993) 213:49-56; development of sulfhydryl-reactive silica for protein immobilization in high-performance affinity chromatography, Mallik et al., Anal Chem (2007) 79:1411-1424; and a sensitive assay for maleimide groups, Singh, Bioconjug Chem (1994) 5:348-351.

SUMMARY OF THE INVENTION

The invention provides assays and methods comprising a dual-enzyme cascade system that is comprised of two enzymatic amplifiers and two molecular probes, which can be used to amplify signal of an enzyme in a biochemical assay and/or a diagnostics assay.

In one aspect the invention provides an amplification assay or method, comprising:

(a) incubating a target/sample enzyme with a target enzyme substrate to liberate a thiol, such as a thiol-containing trigger;

(b) incubating the thiol with a disulfide inactivated amplification enzyme to activate the amplification enzyme in an interchange reaction of the thiol and the disulfide; and (c) incubating the activated amplification enzyme with an amplification enzyme substrate to generate an amplified signal.

In embodiments:

the amplification enzyme is a cysteine protease or a protease modified to provide cysteine protease activity, preferably selected from papain, thioesterases, bromelain, cathepsin K, and calpain, caspase-1 and separase, adenain, pyroglutamyl-peptidase I, sortase A, hepatitis C virus peptidase 2, sindbis virus-type nsP2 peptidase, dipeptidyl-peptidase VI, deSI-1 peptidase, TEV protease, amidophosphoribosylt ransferase precursor, gamma-glutamyl hydrolase, hedgehog protein, and dmpA aminopeptidase;

the target enzyme is a diagnostic enzyme, such as a serum diagnostic enzyme, such as esterase, aldolase, creatine phosphokinase, gamma-glutamyl transpeptidase, lactic dehydrogenase, lipase, transaminases like glutamic-oxaloacetic transaminase and glutamic-pyruvic transaminase, acid phosphatase, alanine aminotransferase, alkaline phosphatase, amylase, angiotensin converting enzyme, aspartate aminotransferase, cholinesterase, lactate, renin, etc;

the target enzyme is pathogenic microbial or viral enzyme, preferably selected from (3-lactamases (particularly carbapenemases), glycosidases (β-D-glucuronidase, β-D-galactosidase, 6-phospho-β-D-galactoside 6-phosphogalactohydrolase, α-D-galactosidase, β-D-glucosidase, α-amylase and α-glucosidase, neuraminidase), esterases and lipases, DNases, peptidases and proteases (pyroglutamyl aminopeptidase, L-alanine aminopeptidase, other aryl peptidases), coagulase, etc.;

the target enzyme substrate is comprises a sulfenyl moiety which is cleaved by the target enzyme to liberate a corresponding thiol, such as such as liberation of an aromatic or alkyl thiol via an elimination mechanism, e.g. phenylsulfanyl liberated to a benzenethiol; and/or the amplification enzyme substrate generates a colored, chemiluminescent, or fluorescent product, such as benzoyl-L-arginine-p-nitroanilide (BAPA) generating 4-nitroaniline or an autocatalytic secondary amplifiers. Secondary autocatalytic amplifiers include peptide and L-arginine derivatives capable of liberating a self-immolative chemical moiety upon hydrolytic cleavage of the backbone peptide, to undergo intramolecular cyclization or elimination mechanisms and evolve additional thiol species to trigger further cysteine proteases or thioesterases.

Self-immolative linker (TYPE I):

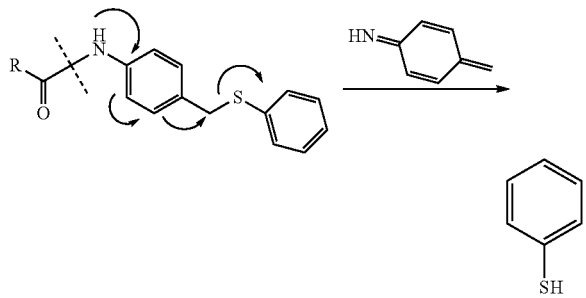

Self-immolative linker (TYPE II):

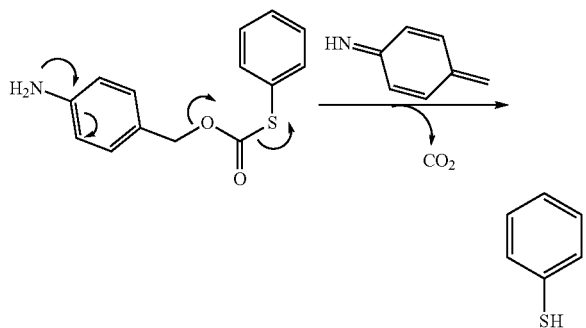

Self-immolative linker (TYPE III, intramolecular cyclization cascade):

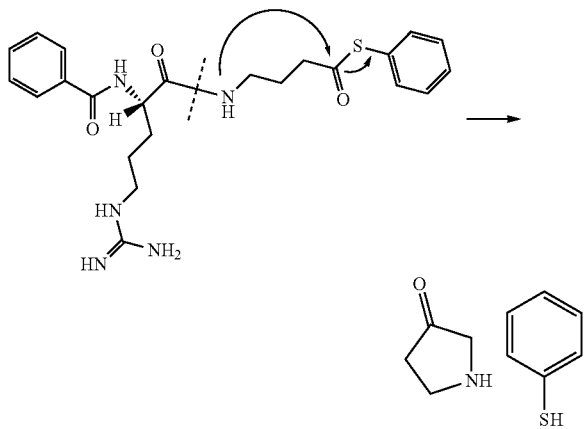

The invention encompasses all combination of the particular embodiments recited herein, as if each combination had been laboriously recited.

BRIEF DESCRIPTION OF THE DRAWINGS

FIG. 1A. Workflow of current empirical treatment practices where urinary tract infections are empirically treated with non-β-lactam or broad-spectrum antimicrobial agents.
FIG. 1B Workflow of the DETECT assay.
FIG. 2B. DETECT amplification is initiated by β-lactamase (Enzyme Amplifier I) hydrolysis of thiophenol-β-lac (E1 Substrate) to liberate the papain trigger thiophenol (E2 Trigger).
FIG. 2C. Thiophenol activates disulfide-protected papain via a disulfide interchange reaction, producing active papain (Enzyme Amplifier II).
FIG. 2D. A colorimetric signal is produced as activated papain molecules hydrolytically cleave the probe BAPA (E2 Substrate).

FIG. 3B. Time-dependent study of β-lactamase activity assay performed with DETECT. FIG. 3C. Photograph of color change observed when the DETECT amplification system is used to measure β-lactamase activity. Study performed in wells of a 96-well plate. FIG. 3D. Time-dependent biochemical experiment, where β-lactamase activity was studied by nitrocefin. FIG. 3E. Comparative assay demonstrating the capacity of DETECT to amplify the signal associated with TEM-1 β-lactamase activity relative to commercially available β-lactamase probe nitrocefin. FIG. 3F. DETECT signal output observed when the activity of recombinant β-lactamases SHV-1, CTX-M-14, CTX-M-15, CMY-2, and KPC-2 were analyzed using DETECT.

FIG. 5B. DETECT diagnostic assay results.
FIG. 5C. DETECT detects ampicillin resistance in clinical urine samples.

DESCRIPTION OF PARTICULAR EMBODIMENTS OF THE INVENTION

Figure 2A:
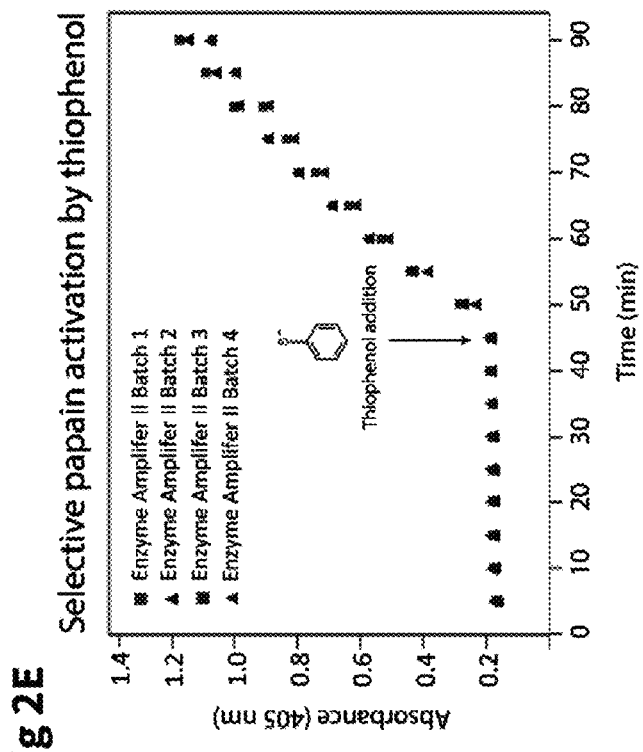
FIG. 2A. DETECT is a two-tiered enzyme amplification technology.

Unless contraindicated or noted otherwise, in these descriptions and throughout this specification, the terms "a" and "an" mean one or more, the term "or" means and/or and polypeptide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

The amplification technology utilizes a dual-enzyme cascade system comprised of two enzymatic amplifiers and two molecular probes. This is exemplified in FIG. 1, wherein the cascade event is initiated when a β-lactamase substrate (thiophenol-β-lac) is hydrolytically cleaved by a β-lactamase to liberate thiophenol, which acts to trigger inactive disulfide-protected papain through a thiol-disulfide interchange reaction. Activated papain (PAPAIN) then completes the amplification cascade by turning over colorimetric probe Nα-benzoyl-L-arginine-p-nitroaniline (BAPA) to afford a turn on in signal.

Hence, in one embodiment, the invention is used for detection of antibiotic resistant determinants, as papain-mediated amplification technology (DETECT). This embodiment provides the unmet need for affordable and rapid point-of-care diagnostic tools in efforts to combat the global epidemic of antibacterial resistance. This embodiment of the technology can identify the presence antibiotic-resistant bacterial strains in unprocessed and untreated urine samples in minutes. The DETECT amplification technology has the ability to significantly amplify signals indicative of β-lactamase activity, circumventing the need for time-consuming and expensive culturing procedures. This technology has been demonstrated to be effective in detecting β-lac in untreated and unprocessed urine samples. Advantages of this technology include: 1) Portability: Our platform can be used in any location, alternative testing methods must be done in a permanent laboratory or medical setting; 2) Low cost of entry: Our platform can packaged as a medical consumable, alternative testing methods require a large initial capital equipment investment; 3) Ease-of-use: Our platform can be used by any medical or lab-staff member trained to handle human blood or urine samples. Alternatives require skilled personnel to operate and often required treatment of biological samples prior to screening; 4) Time-to-results: Our platform can provide results in approximately one hour (or less), compared to 1-3 days for alternative technologies; 5) Room temperature assay: Urinalysis are conducted at room temperature, no need for incubator at any point; 6) Truly no processing required: Whole cell read; no need to lyse cells, no need to concentrate urine, no need to filter; 7) Molecular diagnostic: microscale diagnostic that only requires small volume additions to urine samples; low volume biowaste.

Figure 2E:
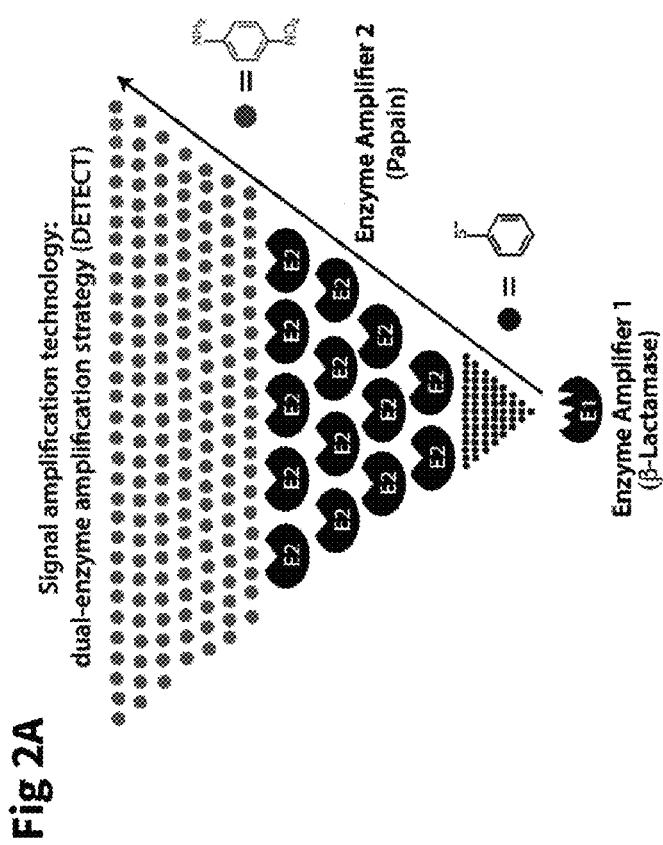
FIG. 2E. Time-dependent plot of absorbance values collected as inactive papain molecules are activated by papain trigger thiophenol, and hydrolytically cleave the probe BAPA (E2 Substrate).

The power of this amplification technology was demonstrated in a randomized double-blinded urinalysis experiment, where resistance determinants were identified in unfiltered and unprocessed urine samples collected from a local medical clinic (FIG. 2). The lack of required culturing and sample preparation, ease of use, colorimetric readout, and low cost make DETECT a viable diagnostic accessory capable of significantly improving antibiotic stewardship and the documentation of antibacterial spread around the world.

We expanded the scope of molecular component 1 (thiophenol-β-lac) by designing and synthesizing alternative β-lactamase probes. To initially validate DETECT a narrow-spectrum probe was utilized that was designed to identify common β-lactamase TEM-1. While TEM-1 continues to be one of the most common β-lactamases conferring resistance in UTI samples, new generations of more lethal β-lactamases have emerged that require alternative therapeutic options. β-lactam resistance variants denoted as extended-spectrum β-lactamases (ESBLs) and carbapenemases represent two classes of β-lactamases that pose great harm to global public health, because the virulence of the β-lactamases that confer these conditions require strict treatment options. However, because non-β-lactam antibiotics, such as ciprofloxacin, are the preferred initial therapeutic option for the treatment of community-acquired UTIs the current diagnostic formulation is capable of identifying β-lactam-sensitive UTIs in the office of a clinician to advance the care of patients and slow the spread of ciprofloxacin resistance.

TABLE 1

Molecular scaffold of second generation β-lactamase ESBL- and carbapenemase-specific probes.

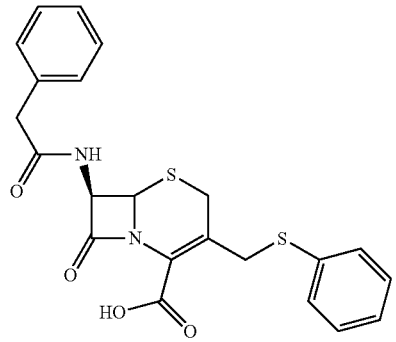

Narrow Spectrum β-Lactamases

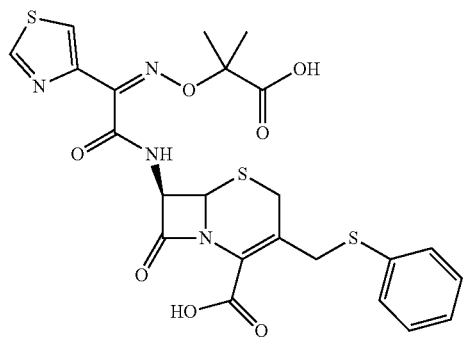

Extended-Spectrum β-Lactamases

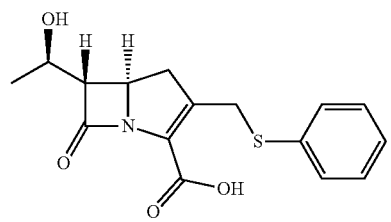

Carbapenem-Resistant Enterobacteriaceae

The papain probe employed in the first-generation DETECT system was commercially available N-benzoyl-L-arginine-p-nitroaniline (BAPA) that is hydrolytically cleaved by papain. Incorporation of BAPA into DETECT afforded powerful signal amplification relative to standard colorimetric β-lactamase probe nitrocefin, showing 3-order magnitude enhancement in β-lactamase detection sensitivity. However, BAPA releases pale yellow chromophore p-nitroaniline as its colorimetric hydrolytic product ($\varepsilon_{410}$=8 800 $M^{-1}cm^{-1}$) and offers suboptimal substrate capacity with papain displaying a $K_{CAT}$ value of 0.7-0.8 $sec^{-1}$, and therefore does not represent the ideal papain probe option.

Table 2 shows alternative papain probes that are capable of visually signaling the presence of resistance determinants in urine samples. We developed two independent synthetic strategies: in the first, the papain probe BAPA is transformed into an autocatalytic component that is capable of evolving secondary thiophenol molecules (AC). The resulting aromatic thiols can then activate additional disfulide-protected papain molecules, introducing a third level of amplification into the DETECT system. In the second, we addressed the suboptimal photophysical properties of chromogenic product by replacing p-nitroaniline with a conjugated benzyl nitrothiophene moiety (BNThio). This chromophore has been incorporated into β-lactam-containing probe that changes from yellow to purple upon hydrolysis of the lactam moiety by β-lac, Ghavami, A. et. al. Anal. Biochem. 486, 75-77 (2015).

TABLE 2

Molecular scaffold of alternative PAPAIN probes.

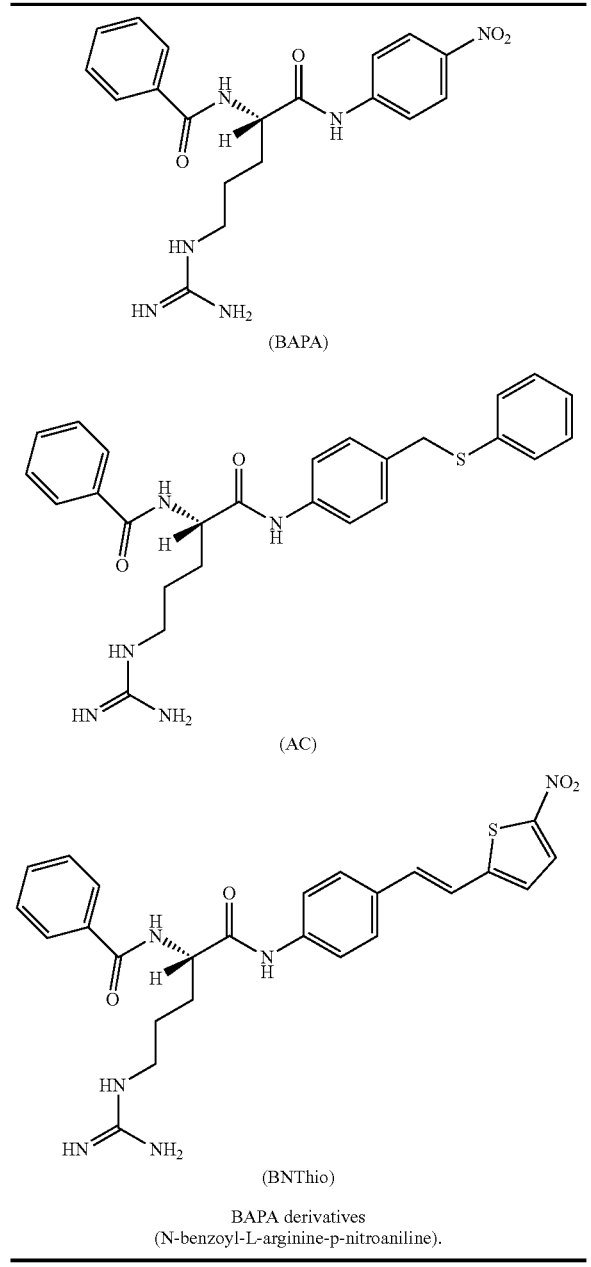

BAPA derivatives
(N-benzoyl-L-arginine-p-nitroaniline).

EXAMPLE

A dual-enzyme amplification technology detects antibiotic resistance in unprocessed clinical urine samples within minutes.

Abstract: The development of resistance to broad-spectrum antimicrobial agents, such as ciprofloxacin and trimethoprim-sulfamethoxazole, is a central problem in medicine, and new strategies for slowing the spread of bacterial resistance to these agents are greatly needed. Point-of-care (POC) assays that can detect β-lactamase activity, to identify patients who could be treated with early-generation β-lactams, have great potential for limiting the use of broad-spectrum antimicrobial agents and slowing the spread of multidrug-resistant bacteria. However, developing POC assays that can detect β-lactamase activity directly in patient samples has been challenging due to the low number of bacteria in clinical samples. To address this need, we developed an instrument-free signal amplification technology, termed DETECT, that circumvents the sensitivity barriers facing traditional β-lactamase-targeted chemical probes. DETECT was designed to identify a wide range of β-lactamases that hydrolyze early-generation β-lactams. We show here that DETECT was able to increase the detection sensitivity of β-lactamase activity by four orders of magnitude compared to the standard chromogenic β-lactamase probe nitrocefin. The DETECT assay was able to detect the hydrolysis activity of a variety of recombinant β-lactamases, and of native β-lactamases produced by clinical isolates of *E. coli* and *K. pneumoniae*. To assess its clinical utility, we performed a validation study using unprocessed urine samples obtained from patients suspected to have a community-acquired urinary tract infection (CA-UTI). DETECT could identify early-generation β-lactam resistance with an accuracy of 0.93 (specificity=0.97 and sensitivity=0.73). We found that 23 (68%) of 34 patients with CA-UTI were infected with *E. coli* susceptible to early-generation β-lactam ampicillin; DETECT thus had the potential to avert the use of alternative broad-spectrum agents in nearly two-thirds of cases of CA-UTI in our study community, where nitrofurantoin and fluoroquinolones are commonly used as first-line empiric therapy.

Introduction: Infections caused by antimicrobial-resistant bacteria are increasing at an alarming rate, and have been recognized by the World Health Organization and Centers for Disease Control and Prevention as an urgent public health concern[1-3]. A key challenge in implementing strategies to curtail the spread of antimicrobial resistance is the lack of point-of-care (POC) assays to rapidly detect antimicrobial resistance[4,5]. Consequently, in many settings, antimicrobial agents are prescribed empirically, which has contributed to the inappropriate use and overuse of these agents.

Community-acquired urinary tract infections (CA-UTIs) represent an infectious disease that would significantly benefit from the development of POC diagnostic tests. CA-UTIs are one of the most common bacterial infections in women, and treatment largely depends on empirical administration of antimicrobial agents[2,6-8]. Ampicillin, an early-generation β-lactam antibiotic, was commonly used for the treatment of CA-UTIs, but was later replaced with broader-spectrum antimicrobial agents due to the development of resistance in CA-UTI patients[9]. However, ampicillin resistance in uropathogenic *Escherichia coli* (UPEC), the most common cause of CA-UTIs, varies from 30% to 50%, depending on the region. This means that ampicillin could potentially be used in 50% to 70% of patients with CA-UTI; however, the inability to obtain susceptibility testing results at the time of a clinic visit precludes its use with high confidence. Currently, determination of an antimicrobial susceptibility profile for UPEC requires time-consuming urine culture and susceptibility testing, which cannot be performed at POC. A POC test that can rapidly rule out ampicillin resistance could reintroduce the use of this relatively inexpensive drug with greater confidence in a substantial proportion of patients with CA-UTI, and spare the use of other agents, such as trimethoprim-sulfamethoxazole, fluoroquinolones, and broader-spectrum β-lactams, to which resistance is increasing among UPEC[10].

β-lactamases are β-lactam-hydrolyzing enzymes and the principal mechanism of resistance to β-lactams in Gram-negative bacteria (GNB), such as UPEC, which makes them an attractive diagnostic target[11-13]. Consequently, there is great interest in developing assays that measure β-lactamase activity, and a variety of fluorescent and chromogenic-based probes and biochemical assays targeting β-lactamases have been developed[14-16]. While β-lactamase probes represent a powerful diagnostic strategy, most tests suffer from poor sensitivity.

Here we report an enzyme amplification technology, termed DETECT that increases the detection sensitivity of an enzyme, e.g. β-lactamase by 40,000 fold. DETECT made it possible to directly measure β-lactamase activity in CA-UTI urine samples to identify patients that could be treated with ampicillin (see FIG. 1B). This amplification technology works by connecting two enzymes together in series, and therefore can be readily used amplify the enzymatic activity of a wide variety of enzymes. As such, DETECT amplifies the detection limit of β-lactamase activity as a strategy to identify β-lactam-resistant UPEC in a POC manner[17] In this report the DETECT diagnostic assay was validated against standard ampicillin susceptibility testing in a randomized double-blinded study and demonstrated 97% specificity, 73% sensitivity, and 93% accuracy. This technology can be used to direct the administration of early-generation β-lactams and spare the use of broad-spectrum antimicrobial agents.

FIG. 1. DETECT can rule out the presence β-lactamase activity in urine samples of patients suspected of having a CA-UTI. By ruling out the presence of β-lactamase activity, physicians can more confidently prescribe ampicillin to spare the use of broad-spectrum antimicrobial agents, decreasing resistance to these agents and extend their lifespan. (A) Workflow of current empirical treatment practices where urinary tract infections are empirically treated with non-β-lactam or broad-spectrum antimicrobial agents. (B) Workflow of the DETECT assay, which will identify ampicillin susceptible patients at the time of care, allowing them to be treated with ampicillin and spare the use of non-β-lactam and broad-spectrum agents.

DETECT harnesses a dual-enzyme amplification strategy to amplify the activity of β-lactamases.

DETECT directs activity amplification of a target enzyme by tethering it to a secondary enzyme using a unique chemical probe (E2-Trigger, FIG. 1A). The overall mechanism of an embodiment of DETECT amplification is shown in FIG. 2A, in which β-lactamase (E1) activates secondary enzymes papain (E2), via chemical probe E2-Trigger, to generate a signal output. DETECT amplifies enzymatic activity because a single β-lactamase enzyme can activate thousands of papain molecules, and each of the activated papain molecules subsequently turns over thousands of its chromogenic substrates, to enhance detection sensitivity by orders of magnitude relative to traditional single-enzyme assays. The strategy relies on the inherent amplification power of enzymes by tethering the target enzyme (β-lactamase) in series with the secondary enzyme amplifier (papain),[17,18] using a unique molecular probe (e.g. thiophenol-β-lac). The detailed chemistry that enables DETECT to amplify β-lactamase activity is shown in FIG. 2B-D. DETECT is a four-component system comprised of: (1) the target enzyme β-lactamase (Enzyme Amplifier 1); (2) papain that has been reversibly inactivated via a disulfide formed with its active site cysteine (Enzyme Amplifier 2); (3) thiophenol-β-lac, which releases the papain trigger thiophenol, after cleavage by β-lactamase; and (4) the papain probe N-benzoyl-L-arginine-p-nitroaniline (BAPA), which releases the colorimetric product nitroaniline.

DETECT-mediated amplification is initiated when a β-lactamase hydrolyzes thiophenol-β-lac and liberates thiophenol, which then activates the disulfide-protected cysteine protease papain, via a disulfide exchange reaction. DETECT amplifies enzymatic activity because a single β-lactamase enzyme can activate thousands of papain molecules, and each of the activated papain molecules can subsequently turn over thousands of BAPA chromogenic substrates, to generate ultrasensitive detection based on a simple colorimetric signal output. The signal output corresponds to p-nitroaniline formation and is observable by eye (yellow hue), and can be quantified using a simple microplate reader (absorbance measured at 405 nm).

FIG. 2. DETECT is comprised of two tiers of enzymatic amplification to enhance the sensitivity for detection of β-lactamase activity. (A) General depiction of the two-tiered amplification technology DETECT, that amplifies the activity of β-lactamase (Enzyme Amplifier 1) by tethering it to the thiol-triggerable enzyme amplifier papain (Enzyme Amplifier 2). (B) DETECT amplification is initiated by β-lactamase (Enzyme Amplifier I) hydrolysis of thiophenol-β-lac (E1 Substrate) to liberate the papain trigger thiophenol (E2 Trigger). (C) Thiophenol activates disulfide-protected papain via a disulfide interchange reaction, producing active papain (Enzyme Amplifier II). (D) A colorimetric signal is produced as activated papain molecules hydrolytically cleave the probe BAPA (E2 Substrate), which generates a colorimetric signal that is visible by eye and measurable by absorption spectroscopy (papain-generated signal measured at an absorbance of 405 nm). (E) Time-dependent plot that depicts the absorbance values collected as inactive papain molecules are activated by papain trigger thiophenol, and hydrolytically cleave the probe BAPA (E2 Substrate). The cleavage of BAPA generates a detectable signal measured at 405 nm.

DETECT targets β-lactamases that confer resistance to early-generation β-lactams and amplifies β-lactamase activity.

Figure 3A:
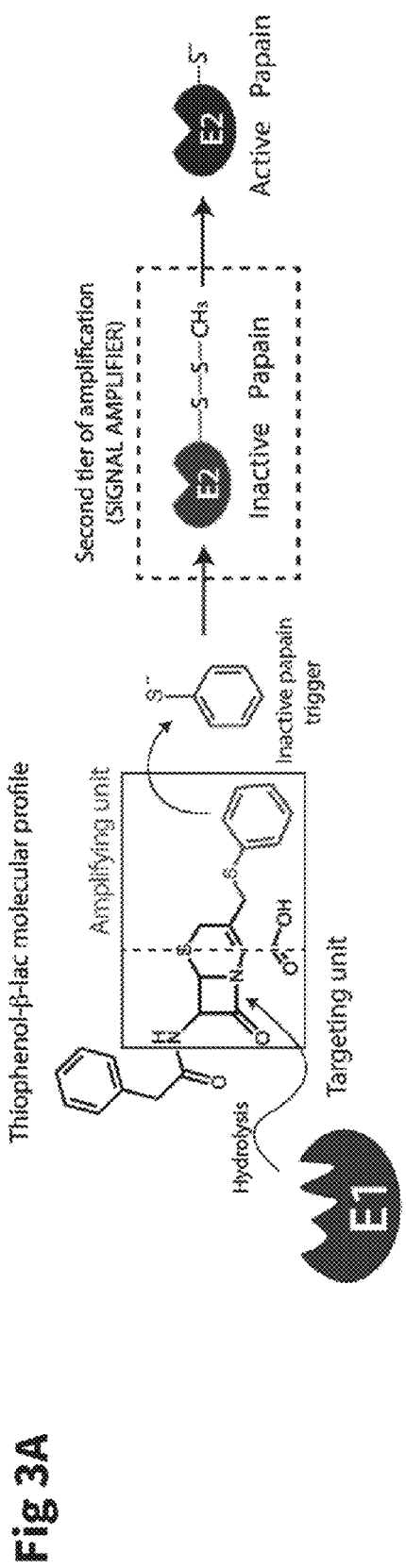
FIG. 3A. The molecular scaffold of thiophenol-β-lac is comprised of a targeting and an amplifying unit.

Thiophenol-β-lac represents the link between the two amplification tiers of DETECT, and contains both a targeting and an amplifying unit (FIG. 3A). The targeting unit features a first-generation cephalosporin core that is vulnerable to hydrolysis by β-lactamases that mediate resistance to early-generation β-lactams. Following hydrolysis of the β-lactam moiety from the targeting unit, the amplifying unit liberates the inactive papain trigger, thiophenol, via a 1,4-elimination cascade (FIG. 2).

To verify the targeting capacity and establish the amplification capacity of thiophenol-β-lac, we first targeted the β-lactamase TEM-1, which mediates resistance to β-lactam antibiotics, such as ampicillin We compared the sensitivity of DETECT against the standard chromogenic β-lactamase probe nitrocefin (FIG. 3)[19]. Recombinant TEM-1 activity was quantified by measuring the formation of the hydrolytic chromogenic products from DETECT or nitrocefin in a time-dependent manner with a microplate reader (DETECT hydrolytic product=405 nm, and nitrocefin hydrolytic product=486 nm). The results from these studies validated the targeting capacity of thiophenol-β-lac and the amplification power of the dual-enzymatic approach of DETECT, which detected 100 fM of TEM-1 compared to nitrocefin's limit of detection at 4 nM TEM-1 (FIGS. 3B and 3D), demonstrating a 40,000-fold enhancement in sensitivity. Furthermore, the plot in FIG. 3E highlights the signal output disparity between DETECT and nitrocefin at 4 nM TEM-1, where DETECT demonstrated a 7-times enhancement in signal output relative to nitrocefin.

We explored if DETECT could also amplify the detection sensitivity of other clinically relevant β-lactamases that mediate resistance to early-generation. We tested the recombinant β-lactamases—SHV-1, CTX-M-2, CTX-M-14, CTX-M-15, CMY-2, and KPC-2—with the DETECT components in a 96-well plate for 30 min. We collected the absorbance at 405 nm in 2 min increments for 30 min, where the final absorbance values at 30 min are shown in FIG. 3F. Results from this study established the molecular promiscuity of thiophenol-β-lac, where the signal outputs from the recombinant β-lactamases SHV-1, CTX-M-2, CTX-M-14, CTX-M-15, CMY-2, and KPC-2 fell within the bounds of the average signal value from TEM-1 (1.1325±0.0566), and SHV-1 exceeded this with a signal output of 1.2377. Therefore, thiophenol-β-lac was validated as an effective probe capable of targeting a broad range of β-lactamases that can hydrolyze early-generation β-lactams.

FIG. 3 Amplification of β-lactamase activity by DETECT requires the targeting capacity of thiophenol-β-lac. (A) The molecular scaffold of thiophenol-β-lac can be divided into two units: the targeting unit and the amplifying unit. The targeting unit of thiophenol-β-lac can be used to target different classes of β-lactamases, while the amplifying unit of thiophenol-β-lac is unique and acts to initiate the second tier of amplification. (B) Time-dependent plot of β-lactamase activity assay performed with DETECT, where varied concentrations of recombinant TEM-1 were incubated with the DETECT system in a 96-well plate for 90 min. The absorbance at 405 nm was collected in 5 min intervals and plotted against time. (C) Photograph of color change caused from DETECT amplification in wells where TEM-1 was present at increasing concentrations from right to left. The rightmost well is a control well where all the components were incubated in the absence of TEM-1. (D) Time-dependent biochemical experiment where varied concentrations of TEM-1 were incubated with the standard β-lactamase probe nitrocefin in a 96-well plate, and the respective absorbance values were collected on a microplate reader (486 nm). (E) Comparative assay demonstrating the capacity of DETECT or nitrocefin to amplify the signal associated with TEM-1 β-lactamase activity, collected after 30 min of incubation. (F) DETECT signal output observed when 500 nM of a recombinant β-lactamase was incubated with the DETECT system for 30 min. Error bars in B, D, and E represent s.d., where n=3.

DETECT amplifies the limit of detection of β-lactamase activity by 3-orders of magnitude relative to the standard β-lactamase probe nitrocefin, in the clinical isolate SF334.

The ability to rapidly detect β-lactamase activity and predict β-lactam resistance in clinical samples remains an unmet clinical need. Currently available chemical probes targeting β-lactamase activity suffer from poor detection limits. Therefore, we sought to define the amplification capacity of DETECT, relative to the standard chromogenic β-lactamase probe nitrocefin, in clinical isolates. We selected an E. coli clinical isolate for testing (SF334), which possessed the TEM-1 β-lactamase encoding gene ($bla_{TEM-1}$) and demonstrated ampicillin and cephalexin resistance on standard susceptibility testing.

Figure 4B:
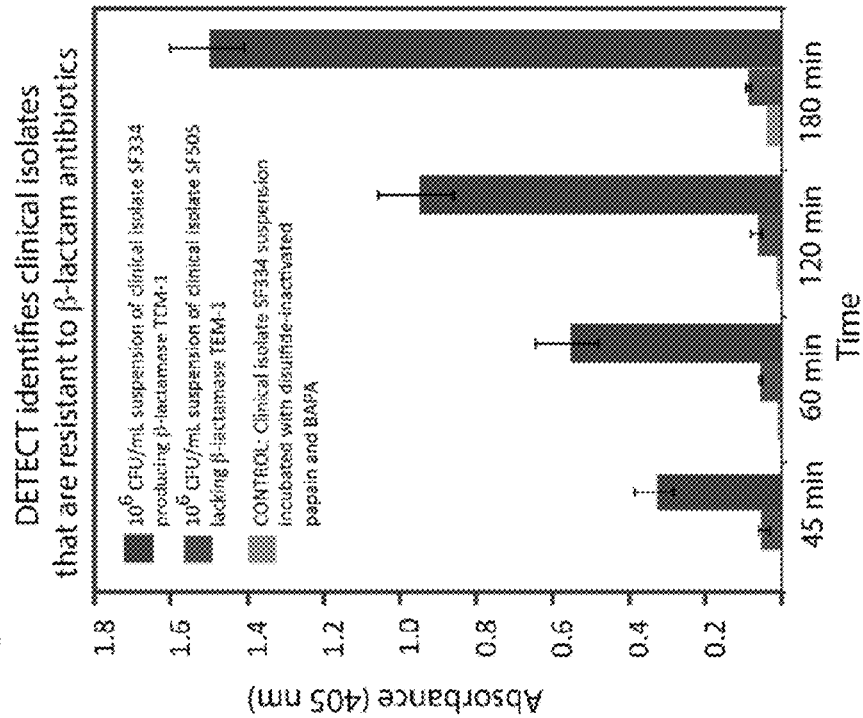
FIG. 4B. Results from a DETECT study.
Figure 4A:
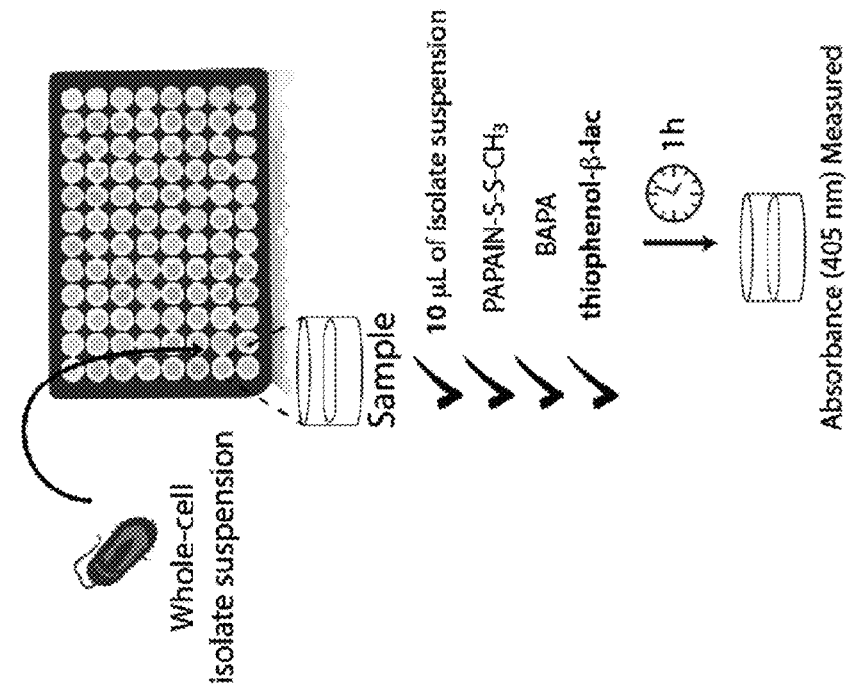
FIG. 4A. Schematic representation of the experiments performed with clinical isolates.

Whole-cell suspensions of SF334 were prepared as described above. First, we confirmed β-lactamase activity in the TEM-1-producing clinical isolate by incubating $10^6$ CFU of SF334 with the DETECT components (FIG. 4A), then collecting absorbance values at 405 nm after 45, 60, 120, and 180 min of incubation. Additionally, a control well was made with $10^6$ CFU of SF334 incubated with inactive papain and BAPA; thiophenol-β-lac was excluded to address the possibility of non-selective activation of thiol-triggered papain by biological thiols that could be present in GNB. As a negative control, we incubated $10^6$ CFU of E. coli clinical isolate SF505, confirmed to be susceptible to β-lactams and lack β-lactamase-encoding genes. Results from this study are highlighted in FIG. 4B, and confirm that DETECT identified β-lactamase activity in SF334. The analogous experiment was performed with nitrocefin, where whole-cell suspensions of SF334 and SF505 were incubated with nitrocefin. As indicated in the literature, samples were incubated with nitrocefin for up to only 30 min to minimize background signal associated with non-selective hydrolysis[14].

Figure 4D:
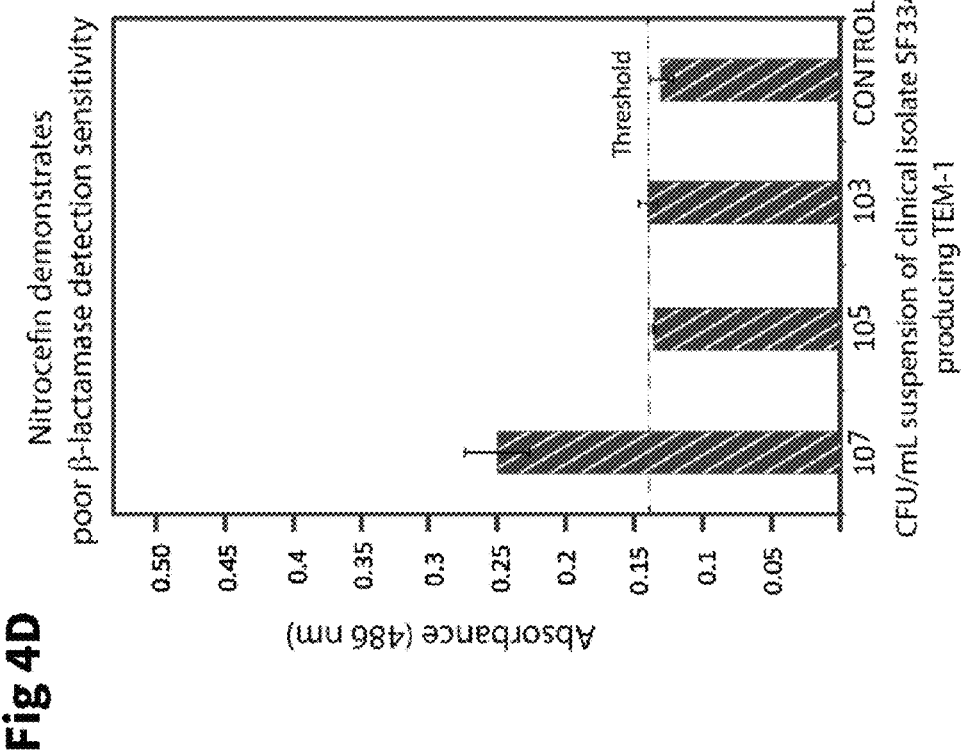
FIG. 4D. Signal threshold of nitrocefin FIG. 5A. Schematic representation of the clinical validation study.
Figure 4C:
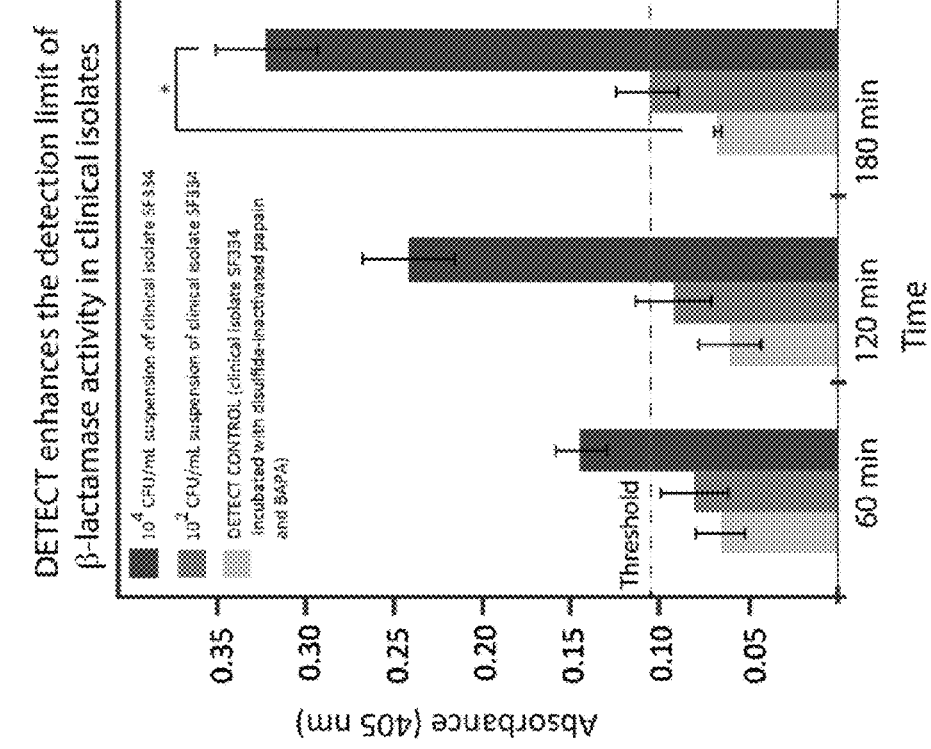
FIG. 4C. Plot displaying the signal outputs generated by DETECT in the presence of varying quantities of b-lactamase-producing clinical *E. coli* isolate SF334.

Subsequent studies were performed to establish the detection limit of DETECT relative to nitrocefin, by serially diluting isolate SF334 in 100-fold increments. Dilutions from $10^6$ CFU/mL down to $10^2$ CFU/mL were made in DETECT wells, and from $10^7$ CFU/mL down to $10^3$ CFU/mL in nitrocefin wells. Results from these studies are shown in FIGS. 4C and 4D, and demonstrate the capacity of DETECT to amplify β-lactamase activity in clinical isolates by 3-orders of magnitude relative to nitrocefin.

FIG. 4. DETECT amplifies the detection limit of β-lactamase activity in clinical isolate suspensions. (A) Schematic representation of the experiments performed with E. coli clinical isolates, where bacterial suspensions were incubated with DETECT components thiophenol-β-lac, disulfide-protected papain, and BAPA in a 96-well plate. Following 1 h of incubation, the sample wells were analyzed with a microplate reader and the absorbance at 405 nm was collected. (B) Results from a preliminary DETECT study where β-lactamase activity in the TEM-1-producing isolate SF334 were compared to the control isolate SF505 (lacking bla genes). The plot highlights the pronounced β-lactamase activity in SF334 and confirms the absence of β-lactamase activity in SF505. (C) Plot displaying the signal outputs generated by DETECT in the presence of varying quantities of SF334, which was carried out to define the signal threshold of DETECT compared to the current standard, nitrocefin. The signal threshold was defined as the minimum signal that was statistically different from the control sample. (D) Similarly, the signal threshold of nitrocefin was determined by incubating nitrocefin with the represented CFU/mL and recording the absorbance at 486 nm after 30 min Error bars in B, C, and D represent s.d. where n=3.

DETECT can detect β-lactamase activity in clinical isolates and predict ampicillin resistance in clinical isolates.

To further investigate the clinical potential of DETECT, we explored the ability to detect β-lactamase activity in a panel of clinical isolates resistant to early-generation β-lactams. Since E. coli and Klebsiella pneumoniae are the predominant pathogens associated with CA-UTIs, we selected these isolates with ampicillin and/or cephalexin resistance, as assessed by standard disc diffusion tests[21-23]. Further attempts were made to select isolates that produced only a single β-lactamase variant, to clearly identify β-lactamases capable of triggering the DETECT system in clinical isolate suspensions.

Bacterial suspensions of clinical isolates were prepared from overnight broth cultures to a final optical density at 600 nm (OD 600 nm, where 1 OD=1.0×10⁸ CFU/mL) of 0.6 (±0.02). Ten μL of each whole-cell bacterial suspension were transferred to two wells of a 96-well plate, each containing BAPA solution and inactive papain solution. The incubation time was initiated when thiophenol-β-lac was added to one of the two samples wells, where the second well was used as a control to evaluate non-specific background signal. After a 1 h incubation period, the absorbance value at 405 nm was collected with a microplate reader. Subsequently, the change in the 405 nm absorbance ($\Delta\lambda_{405}$) from time 0 to 1 h was calculated for both sample and control wells, denoted as "DETECT Score" in Tables 1 and 2. To utilize the DETECT score as an indicator for phenotypic resistance to ampicillin or cephalexin in clinical isolates, we established a threshold value of 0.2627; this was 3 standard deviations greater than the average $\Delta\lambda_{405}$ of control wells. Therefore, samples with DETECT scores <0.2627 were denoted as negative (−), and samples with scores >0.2627 were denoted as positive (+). If the DETECT score was in agreement with ampicillin or cephalexin susceptibility results, the DETECT result was interpreted as "TRUE"; disagreement was interpreted as "FALSE".

TABLE 1

Results of β-lactamase detection assay DETECT, to establish the capacity of DETECT to identify β-lactamase activity in clinical isolates of *E. coli*. The sample identification number and resistance features for each β-lactamase-producing *E. coli* isolate are listed.

| Isolate ID | β-lactamase gene | Result | Ampicillin susceptibility | Verification (ampicillin) | Cephalexin susceptibility | Verification (cephalexin) |
|---|---|---|---|---|---|---|
| SF384 | ND | − | S | TRUE | S | TRUE |
| SF105 | TEM-1 | + | R | TRUE | R | TRUE |
| BE372 | TEM-1 (1b) | + | R | TRUE | R | TRUE |
| BE1004 | TEM-1 (1c) | + | R | TRUE | S | FALSE |
| BE1173 | TEM-1 (1b) | + | R | TRUE | S | FALSE |
| BE527 | SHV-1 | + | R | TRUE | S | FALSE |
| BE30 | SHV-1 | + | R | TRUE | S | FALSE |
| BE1335 | SHV-1 | + | R | TRUE | S | FALSE |
| BE115 | OXA-1 | + | R | TRUE | S | FALSE |
| SF487 | CTX-M-14 | + | R | TRUE | R | TRUE |
| SF148 | CTX-M-14 | + | R | TRUE | R | TRUE |
| SF410 | CTX-M-15 | + | R | TRUE | R | TRUE |
| SF674 | CTX-M-15 | + | R | TRUE | R | TRUE |
| SF141 | CMY-2 | + | R | TRUE | R | TRUE |
| SF207 | CMY-2 | + | R | TRUE | R | TRUE |
| BR2 | KPC-2 | + | R | TRUE | R | TRUE |

The DETECT score, defined as the change in 405 nm absorbance of the sample from time t = 0 to t = 1 h, for each isolate was designated as negative (−) or positive (+) based on a threshold, and verified as "TRUE" or "FALSE" according to the phenotypic susceptibility of the isolate to ampicillin or cephalexin. ND, none detected; S, susceptible; R, resistant.

TABLE 2

Results of β-lactamase detection assay DETECT, to establish the capacity of DETECT to identify β-lactamase activity in clinical isolates of *K. pneumoniae*. The sample identification number and resistance features for each β-lactamase-producing *K. pneumoniae* isolate are listed.

| Isolate ID | β-lactamase gene | Result | Ampicillin susceptibility | Verification (ampicillin) | Cephalexin susceptibility | Verification (cephalexin) |
|---|---|---|---|---|---|---|
| SF412 | ND | − | S | TRUE | S | TRUE |
| SF519 | ND | − | S | TRUE | S | TRUE |
| BR313 | SHV-83/187 | + | R | TRUE | S | FALSE |
| BR45 | SHV-38/168 | + | R | TRUE | S | FALSE |
| BR50 | SHV-62 | + | R | TRUE | S | FALSE |
| BR27 | SHV-11 | + | R | TRUE | S | FALSE |
| BR52 | SHV-132 | + | R | TRUE | S | FALSE |
| BR1 | SHV-185 | + | R | TRUE | S | FALSE |
| BR28 | KPC-2, SHV-11 | + | R | TRUE | R | TRUE |
| ATCC 700603 | SHV-18 (ESBL) | + | R | TRUE | R | TRUE |

The DETECT score, defined as the change in 405 nm absorbance of the sample from time t = 0 to t = 1 h, for each isolate was designated as negative (−) or positive (+) based on the threshold value, and verified as "TRUE" or "FALSE" according to the phenotypic susceptibility of the isolate to ampicillin or cephalexin. ND, none detected; S, susceptible; R, resistant; ESBL, extended-spectrum β-lactamase.

The results collected with the DETECT diagnostic assay were compared to results collected by standard susceptibility testing to verify the capacity of DETECT to identify β-lactamase activity and predict resistance to the early-generation β-lactams, ampicillin and cephalexin, in *E. coli* and *K. pneumoniae* clinical isolates, as shown in Table 1 and 2. The DETECT diagnostic assay correctly identified all of the *E. coli* and *K. pneumoniae* isolates producing β-lactamases that mediate resistance to ampicillin or cephalexin (Table 1 and Table 2). Interestingly, the isolates with an identified β-lactamase gene were resistant to ampicillin, but not necessarily to cephalexin; as a consequence, DETECT results served as a more accurate indicator of ampicillin resistance than cephalexin resistance. These findings demonstrate the use of our methods and of thiophenol-β-lac to confidently reveal β-lactamase activity in clinical isolates and direct the treatment of CA-UTIs, allowing the early-generation β-lactam, ampicillin, to be used in place of other agents.

DETECT can identify β-lactam resistance in unprocessed clinical urine samples.

DETECT was further explored as a diagnostic assay for detecting early-generation β-lactam resistance directly from clinical urine samples containing UPEC. In a randomized double-blinded validation study, 40 clinical urine samples were studied. Samples were collected from the outpatient clinic at the University of California, Berkeley. No personal identifiers or clinical information were obtained from the study subjects, but most of the patients were women students on campus. The urine samples were screened at the health center by dipstick, and those testing positive for leukocytes, nitrates, protein, blood, or glucose were used in this study.

Urine samples were analyzed by DETECT, as described in FIG. 5A, where two 50 μL aliquots of each urine sample were transferred into two independent wells on a 96-well plate, designated "sample" and "control". Urine samples in sample wells were incubated with all DETECT components, while corresponding urine samples in control wells were incubated with inactive papain and BAPA to rule out non-specific reactions that could be triggered by free thiols or proteases. All samples were incubated for 30 min at room temperature and then analyzed on a microplate reader at 405 nm. For each sample, a $\Delta\lambda_{405}$ value was calculated by taking the difference in the 405 nm absorbance values at time 0 and 30 min.

In order to establish the threshold $\Delta\lambda_{405}$ of DETECT, that delineates β-lactam-susceptible from β-lactam-resistant urine samples, we simultaneously analyzed urine samples by traditional microbiology techniques as a standard for comparison (raw $\Delta\lambda_{405}$ of DETECT values shown in Table S1). As such, urine samples were cultured for identification of *E. coli*, and *E. coli* isolates were tested for susceptibility to ampicillin and cephalexin. Samples were separated for analyses based on susceptibility or resistance to these agents, and an average $\Delta\lambda_{405}$ value was calculated for each group. The average $\Delta\lambda_{405}$ values corresponding to β-lactam-resistant and β-lactam-susceptible samples are shown in FIG. 5B, where the average $\Delta\lambda_{405}$ of samples defined by traditional susceptibility analyses as resistant to ampicillin or cephalexin was 1.026, and the average $\Delta\lambda_{405}$ in samples containing susceptible *E. coli* was 0.2990 (p=0.00048, two-tailed t-test). Finally, the threshold value was defined as 0.616, three standard deviations greater than the average $\Delta\lambda_{405}$ of β-lactam-susceptible isolates. Therefore, samples with $\Delta\lambda_{405}$>0.616 were defined as "positive" by DETECT (or resistant to early-generation β-lactams), and samples with $\Delta\lambda_{405}$<0.616 were defined as "negative" by DETECT (or susceptible to β-lactams), the latter of which would qualify for treatment with an early-generation β-lactam.

FIG. 5. DETECT can detect ampicillin resistance in clinical urine samples. (A) Schematic representation of the clinical validation study where 50 μL of a urine sample was added to a well of a 96-well plate. After 30 min of incubation of urine with the DETECT components, the absorbance was measured at 405 nm on a microplate reader. (B) DETECT diagnostic assay results, demonstrating the difference between the average $\Delta\lambda_{405}$ signals from ampicillin-resistant and ampicillin-susceptible urine samples. Urine samples were categorized as resistant or susceptible based on standard susceptibility testing results from their corresponding isolated UPEC (p=0.00048, two-tailed t-test). (C) Of the 40 urine samples used in this study, 34 contained UPEC. Eight of 11 UPEC were identified correctly by DETECT to contain β-lactamases that direct resistance to early-generation β-lactams, and 28 of 29 samples lacking β-lactamase activity were correctly identified by DETECT. Nearly two-thirds of the *E. coli* isolated from CA-UTI samples were susceptible to ampicillin, and would therefore qualify for treatment with this agent or another early-generation β-lactam.

The investigator performing the DETECT assay was blinded to the microbiology results, and the investigators performing the microbiology tests were blinded to the DETECT results. When compared to standard microbiology analysis (UPEC identification and susceptibility testing), the DETECT assay identified β-lactam resistance in unprocessed clinical urine samples in 8 (73%) of 11 samples containing ampicillin- or cephalexin-resistant *E. coli*, and in one of the 29 samples identified to be negative for *E. coli* or contain ampicillin- or cephalexin-susceptible *E. coli*. Based on this data, the sensitivity, specificity and accuracy of the DETECT assay were 0.73, 0.97, and 0.93, respectively (p=0.00048). The false negative and false positive samples were further analyzed to determine if the erroneous predictions were due to low bacterial counts in the urine. The bacterial isolates from the four urine samples that generated false negative or positive results were tested at $10^6$ CFU/mL with DETECT, following the procedure reported above. Results from this study confirmed that all samples elicited a signal output indicative of β-lactamase activity.

Culturing of the 40 urine samples revealed that 34 samples contained *E. coli*. Interestingly, 23 (68%) of 34 *E. coli* isolated from these consecutively collected CA-UTI samples from October 2016 to March 2016 were susceptible to ampicillin, by both standard susceptibility testing and DETECT testing. Thus, at this clinic, the use of DETECT could have enabled treatment with ampicillin or a first-generation cephalosporin in nearly ⅔ of the CA-UTI patients, sparing the unnecessary use of broader-spectrum antibiotics.

Diagnostic tools with the capacity to identify patients that can be treated with early generation β-lactams have the potential to significantly lower the rate at which bacteria become resistant to broader-spectrum agents. In particular, the lack of rapid diagnostic tests to inform appropriate antibiotic selection for treatment of CA-UTIs remains an important unmet need, and forces clinicians to prescribe broad-spectrum antimicrobial agents empirically. This practice contributes to the selection of multidrug-resistant UPEC. We have developed and disclosed here a POC assay capable of providing clinicians with diagnostic information that enables treatment of CA-UTIs with early-generation β-lactams, to avert the use of broad-spectrum agents when possible. The application of this assay can be readily applied to rapidly and inexpensively detect early-generation β-lactam resistance in hospital-acquired UTIs or bloodstream infections caused by GNB.

While diagnostic assays that target β-lactamases are widely recognized as an attractive diagnostic approach, translation of these technologies into clinical use has been impeded by poor sensitivity. Here, we addressed the technological challenges facing β-lactamase-targeted assays by harnessing the amplification power of enzymes. Initial validation studies conducted with recombinant TEM-1 β-lactamase showed DETECT to be 40,000-fold more sensitive compared to the standard chromogenic probe nitrocefin, enabling the detection of 100 fM TEM-1. Additional validation studies with a TEM-1-producing clinical isolate (SF334) demonstrated that DETECT generated a three orders of magnitude enhancement in detection sensitivity, and could identify β-lactamase activity in a $10^4$ CFU/mL suspension of SF334 (well within the range of CFU found in CA-UTI urine samples), compared to nitrocefin that required $10^7$ CFU/mL to elicit a signal above background signal.

The β-lactam probe of DETECT (thiophenol-β-lac) features a promiscuous first-generation cephalosporin molecular core, which is designed to identify β-lactamases that confer resistance to early-generation β-lactams. As predicted, thiophenol-β-lac was vulnerable to hydrolysis by a wide array of recombinant β-lactamases, ranging from TEM-1 to the more broad-spectrum β-lactamase, KPC-2. Subsequent experiments were performed to validate the β-lactamase-targeting capacity of thiophenol-β-lac, by analyzing clinical isolates possessing a single β-lactamase. Results from these studies demonstrated a semi-quantitative feature of DETECT, where clinical isolates producing broad-spectrum β-lactamases that confer resistance to third- and fourth-generation cephalosporins or carbapenems (namely CTX-Ms, CMY, and KPC), elicited a significantly stronger chromogenic signal than isolates producing β-lactamases that confer resistance to early-generation β-lactams only, such as TEM-1 and SHV-1.

Finally, validation of the DETECT diagnostic assay was performed with 40 urine samples collected from patients suspected of CA-UTI at the outpatient clinic at the University of California, Berkeley. DETECT was able to accurately ascertain the lack of β-lactamase activity and β-lactam resistance in 22 of the 23 urine samples containing β-lactam-susceptible UPEC (negative predictive value of 96%). In general, outpatient clinics commonly prescribe non-β-lactams nitrofurantoin or fluoroquinolones empirically to treat CA-UTI. However, 68% of the UPEC isolated from this clinic were susceptible to ampicillin, and therefore ⅔ of the UTI could have been treated with ampicillin, sparing the use of non-β-lactam antibiotics. The need for curtailing the use of fluoroquinolones in particular is compelling, given that resistance to fluoroquinolones is increasing in CA-UTI UPEC strains around the world[9].

The sensitivity of DETECT with clinical urine samples was 73%, where eight of 11 UPEC isolated from these samples and identified as ampicillin- or cephalexin-resistant by susceptibility testing were detected with our assay. Genetic analysis of the 11 β-lactam-resistant UPEC revealed that 10 (91%) of the isolates produced TEM-1 and three (27%) of the isolates produced a CTX-M β-lactamase (from CTX-M-g1 and CTX-M-g9). Two of the three urine samples that were missed by DETECT were later found to contain UPEC producing TEM-1, while the third isolate was found to contain UPEC producing TEM-1 and a CTX-M-g9 enzyme (likely CTX-M-14). Because DETECT accurately identified these β-lactamases in other clinical isolates and demonstrated the capacity to detect β-lactamase activity in as little as $10^3$ CFU of TEM-1-producing clinical isolate SF334, it is likely that the concentration of bacteria in the missed urine samples fell below the clinical limit of detection. Further, the UPEC isolated from the three missed urine samples were subsequently tested with DETECT and found to be positive, with an average $\Delta\lambda_{405}$ of 1.281, ranging from 0.7232 to 2.542.

We have demonstrated the power of the DETECT to amplify enzyme activity in clinical urine samples. Importantly, DETECT was able to rapidly and inexpensively identify β-lactamase activity in clinical urine samples without sample processing or culturing, demonstrating the potential to function as a POC assay for identifying β-lactam resistance. Innovative diagnostic assays like DETECT enable clinicians make informed treatment decisions at POC, to direct the appropriate administration of antimicrobial agents while minimizing the selection of antimicrobial-resistant bacteria. In contrast to other biochemical approaches that measure changes in pH as an indirect measure of β-lactamase activity, DETECT utilizes a direct approach that tethers β-lactamase activity to the enzyme amplifier papain, through the unique β-lactamase probe thiophenol-β-lac[25,26]. This strategy enables detection of β-lactamase activity in clinical urine samples without sample processing or culturing.

While initial efforts were aimed at developing a POC diagnostic to direct the treatment of CA-UTIs—mainly to rule in the use of early-generation β-lactams as a viable treatment option—broader-spectrum β-lactamases, which are more frequently identified in hospital-acquired infections, can easily be targeted by simply replacing the molecular core of thiophenol-β-lac with one analogous to a third- or fourth-generation cephalosporin or a carbapenem.

REFERENCES

Sugden, R., Kelly, R., & Davies, S., Nat. *Microbiol.* 1, 1-2 (2016).
Perez, K. K., et. al. *Journal of Infection.* 69. 216-225 (2014).
Goff, D. A., et. al., *Lancet Infect. Dis.* 17, e56-e63 (2017).
Galar, A., et al. *Journal of Infection.* 65. 302-309 (2012).
Blascke, A. J., et. al. *Diagn. Microbiol. Infect. Dis.* 81, 57-59 (2015).
Badder, M. S., Loeb, M., & Brooks A. A. *Postgrad. Med.* 129, 242-258 (2017).
Vasudevan, R. *J. Microbiol. Exp.* 1, 1-15 (2014).
Flores-Mireles, A. L., et al, *Nat. Rev. Micro.* 13, 269-284 (2015),
Gupta, K., et. al. *Clin. Infect. Dis.* 52, 103-120 (2011).
M. Kessel, *Nat. Biotechnol.* 33, 898-900 (2015).
Biehl, L. M., et. al. *Crit. Rev. Mircobiol.* 42, 1-16 (2016).
Partridge, S. R. *Pathol.* 47, 276-284 (2015).
Jacquier, H., et. al. *Proc. Natl. Acad. Sci.* 110, 13067-13072 (2013).
O'Callaghan, C. H., et al., *Antibicrob. Agents Chemother.* 1, 283-288 (1972).
Johnson, J. R. & O'Bryan, T. T. *Clin. Diagn. Lab Immunol.* 7, 265-273 (2000).

Kie, H., et. al. *Nat. Chem.* 4, 802-809 (2015).
Singh, R., et al., *Analytical Biochemistry.* 213. 49-56 (1993).
Brocklehurst, K., et al, *The Biochemical Journal.* 133. 67-80 (1973).
Brocklehurst, K., Little, G. *The Biochemical Journal.* 128. 471-474 (1972).
Dallenne, C., et al. *J. Antimicrob. Chemother.* 65, 490-495 (2010).
Tarlton, N. J., et al. *J. Microbiol Methods,* 144, 37-43 (2018).
Adams-Sapper, S., et al., *Antimicrob. Agents. Chemother.* 57, 490-497 (2013)
Adams-Sapper, S., et al., *Antimicrob. Agents Chemother.* 59, 3281-3289 (2015).
Smith, S. P., et al. *Clin. Infect. Dis.* 46, 689-695 (2008).
Morosini, M. I., et al., *J. Clin. Microbiol,* 52, 1741-1744 (2014)
Renvoisé, A. e. al. *J. Clin. Microbiol,* 51, 4012-2017 (2013).

The invention claimed is:

1. An assay method to determine the presence of a β-lactam resistant bacterium in a sample from a subject, the method comprising:
   obtaining the sample from the subject;
   incubating the sample with reaction components comprising:
   (i) a β-lactamase probe having a structure selected from the group consisting of:

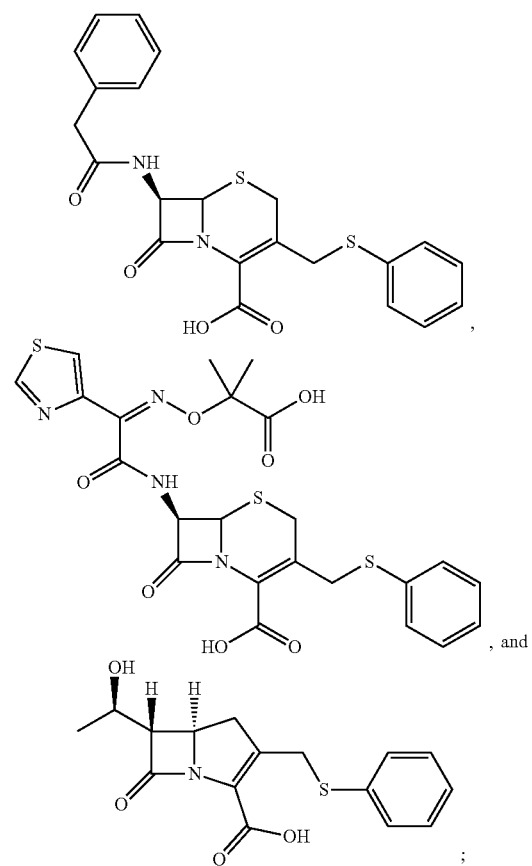

(ii) papai-S—S—CH$_3$; and (iii) a papain probe having a structure
selected from the group consisting of:

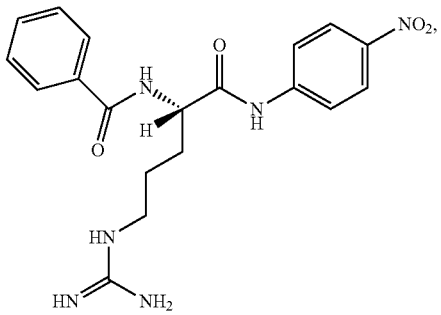

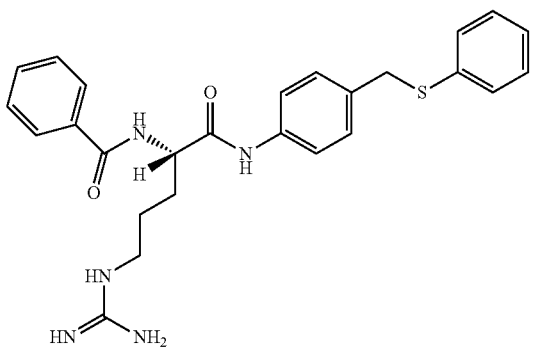 [SMILES: N=C(N)NCCC[C@H](NC(=O)c1ccccc1)C(=O)Nc1ccc(CSc2ccccc2)cc1]

, and

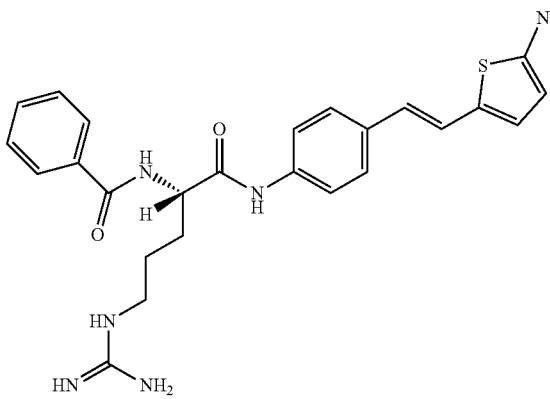

and determining the generation of a colorimetric signal from incubating the sample with the reaction components by visual inspection of the sample or by absorption spectroscopy, wherein the absorption spectroscopy is carried out at a wavelength of 405 nm;

wherein, the colorimetric signal which has been generated from the incubated sample indicates that the subject's sample comprises a β-lactam resistant bacterium, wherein the sample that is obtained from the subject is an unprocessed urine sample, wherein the unprocessed urine sample is obtained from a subject that has, or is suspected of having, a urinary tract infection, and wherein the sample is incubated with the reaction components at room temperature.

* * * * *